US012806241B2

(12) United States Patent
Cooper Eames Helleger

(10) Patent No.: US 12,806,241 B2
(45) Date of Patent: Nov. 24, 2026

(54) EXTRACTION OF CANNABINOIDS, FLAVONOIDS AND TERPENES FROM CANNABIS

(71) Applicant: SILVER STALLION GMBH, Sarnen (CH)

(72) Inventor: Gordon Cooper Eames Helleger, Nevada City, CA (US)

(73) Assignee: SILVER STALLION GMBH, Sarnen (CH)

( * ) Notice: Subject to any disclaimer, the term of this patent is extended or adjusted under 35 U.S.C. 154(b) by 869 days.

(21) Appl. No.: 17/603,650

(22) PCT Filed: Jul. 12, 2019

(86) PCT No.: PCT/IN2019/050520

§ 371 (c)(1),
(2) Date: Oct. 14, 2021

(87) PCT Pub. No.: WO2020/212999

PCT Pub. Date: Oct. 22, 2020

(65) Prior Publication Data

US 2022/0233619 A1 Jul. 28, 2022

(30) Foreign Application Priority Data

Apr. 17, 2019 (IN) ............................. 201921015397

(51) Int. Cl.

| | |
|---|---|
| ***A61K 36/185*** | (2006.01) |
| ***A23L 33/105*** | (2016.01) |
| ***A61K 31/00*** | (2006.01) |
| ***B01D 11/02*** | (2006.01) |

(52) U.S. Cl.
CPC ........ *A61K 36/3482* (2024.05); *A23L 33/105* (2016.08); *A61K 31/658* (2023.05); *B01D 11/0269* (2013.01); *B01D 11/0288* (2013.01); *A23V 2002/00* (2013.01); *A61K 2236/15* (2013.01); *A61K 2236/37* (2013.01); *A61K 2236/53* (2013.01)

(58) Field of Classification Search
CPC .............. A61K 36/185; A61K 2236/15; A61K 2236/53; A23L 33/105; B01D 11/0269; B01D 11/0288; A23V 2002/00
See application file for complete search history.

(56) References Cited

U.S. PATENT DOCUMENTS

2003/0050334 A1 3/2003 Murty et al.
2018/0344785 A1 12/2018 Robertson

FOREIGN PATENT DOCUMENTS

WO 2004016277 A2 2/2004
WO WO 2016187679 * 12/2016 ........... A61K 36/185

OTHER PUBLICATIONS

ISA/IN "International Search Report for PCT/IN2019/050520", India, Oct. 11, 2019.

* cited by examiner

*Primary Examiner* — Trevor Love
(74) *Attorney, Agent, or Firm* — Tim Tingkang Xia, Esq.; Troutman Pepper Locke LLP

(57) ABSTRACT

The present invention relates to a process for preparing an extract from *Cannabis* comprising an extraction step of treating the *Cannabis* with carbon dioxide at a temperature of between 0° C. to 15° C. and a pressure between 1250 psi and 1600 psi to obtain an extract; and centrifuging the extract between 20° C. to 40° C.

1 Claim, No Drawings

EXTRACTION OF CANNABINOIDS, FLAVONOIDS AND TERPENES FROM CANNABIS

FIELD OF THE INVENTION

This invention generally relates to a method of extracting natural products from a plant or plant material. More particularly, the invention relates to a method of extracting cannabinoids, flavonoids and terpenes from a *Cannabis* genus of plant.

BACKGROUND OF THE INVENTION

Cannabinoid-containing plant extracts are in high demand due to the medicinal value and other applications and may be obtained by various means of extraction of *Cannabis* plant material. Such means include but are not limited to: supercritical or subcritical extraction with carbon dioxide (CO2), extraction with hot gas and extraction with solvents. These methods, which are known by those skilled in the art, are deficient for many reasons.

One problem with the supercritical carbon dioxide extraction is that the cost of the equipment makes it cost-prohibitive. It is also done under high pressure (2000-5000 psig, or pounds per square inch gage), which is generally detrimental to the quality and yield of the final product extract. The method also produces low purity extract (30-70% pure THC, 3-10% by weight of the plant) (Murry et al, US Publication No. 2003/0050334) and there is also a significant amount of water that binds to the THC. Another drawback to supercritical CO2 extraction is that it is performed in small batches. Each batch can take up to eight hours to complete. Also, and similar to non-polar solvent extraction methods, the extract is further purified by refinement necessary to remove components of the concentrate which are not desirable for primary medical applications, such as lipids, waxes and residual moisture, all of which dilute the active compounds, such as cannabinoids, terpenoids and flavonoids, and compromise the concentrate by hastening its degradation.

The terpene and flavonoid components of *Cannabis* have medical value, and are used in many medical preparations, but their concentration is low in typical CO2 extraction methodologies for multiple reasons. This is largely due to the relatively low volatility points of most terpenes and flavonoids commonly found in *Cannabis,* and their volatilization makes their concentration impractical under typical CO2 parameters and refinement processes.

The refinement methodologies typically applied to CO2 concentrates further disturb and dilute the presence of terpene and flavonoid compounds in resultant, refined *Cannabis* concentrates. This is due to the exposure of the concentrate during refinement, to temperatures in excess of the volatility points of the aromatic compounds, thus, degradation takes place if the compounds are re-captured, or they are completely lost and no longer components of the refined concentrate. These conditions are necessary when using typical methods which require the addition and subsequent removal of a secondary solvent. To achieve solvent volatilization for removal from the concentrate, the volatility points of the terpenes and flavonoids are exceeded and thus, at best, degradation takes place if the compounds are re-captured, or they are completely lost through the process of purging the solvent and are no longer components of the refined concentrate. If the solvent is not volatilized and purged, the quality of the concentrate is greatly diminished and potentially hazardous, because of the unavoidable levels of residual solvent retained within the concentrate itself.

A cheaper and safer extraction of cannabinoid from a *Cannabis* genus of plant is desired. The process should ideally produces a high overall yield of extract comprising cannabinoid, along with flavonoids and terpenes. It is further desired that the extract contains substantially no waxes, resins or other undesirable compounds. Thus, a methodology of concentration, which maintains as much of the plant's complete spectrum of active compounds as possible, has no residual solvent and is of high purity, is needed to be developed.

SUMMARY OF THE INVENTION

In one aspect, the invention provides a solvent-free process for preparing an extract from *Cannabis* comprising

- an extraction step of treating the *Cannabis* with carbon dioxide at a temperature of between 0° C. to 15° C. and a pressure between 1250 psi and 1600 psi to obtain an extract; and
- centrifuging the extract between 20° C. to 40° C.

In another aspect, the invention provides a *Cannabis* extract comprising cannabinoid in a range of 30-75%, terpenes in a range of 5-35% and flavonoids.

DESCRIPTION OF THE INVENTION

The present invention is directed towards a process for preparing an extract from *Cannabis* and the extract prepared therefrom, wherein the extract is a high-purity refined *Cannabis* concentrate which is rich in cannabinoids, flavonoids, terpenes, and provides a broad-spectrum of the original plant-based compounds. This process ensures the most minimal degradation of volatile plant-based compounds.

In one aspect, the present invention provides a process for preparing an extract from *Cannabis* comprising

- an extraction step of treating the *Cannabis* with carbon dioxide at a temperature of between 0° C. to 15° C. and a pressure between 1250 psi and 1600 psi to obtain an extract; and
- centrifuging the extract between 20° C. to 40° C.

In this regard, extraction step is followed by a decarboxylation step preferably between 115° C. to 14o° C. and then centrifugation at 16° C. to 27° C. These parameters allow for a comprehensive spectrum of the cannabinoid, terpenoid and flavonoid profiles of the plant matter to be concentrated effectively without the de-naturing that takes place at higher temperatures and pressures. Also, the extraction process that occurs under these parameters leaves much of the waxes and lipids behind in the plant matter and does not include them in the resultant concentrate, thus facilitating future refinement.

In an embodiment of the invention, the centrifuging is conducted in a refrigerated centrifuge resulting in a mechanical separation of the components of the concentrate. Lipids, waxes and moisture will separate from the desired concentrate material without de-naturing the aromatic profile, as long as the temperatures are strictly controlled. In this regard, the centrifuging typically takes place over a series of cycles through the centrifuge with RPM's between 5,000 and 12,000 and durations between 30 minutes and 6 hours. The temperature range of between 20° C. and 40° C., ideally utilizes increasing temperature and pressure in subsequent cycles, once the more easily separated components are removed to minimize their exposure to higher temperatures.

By carefully controlling the temperature and pressure below the super-critical temperature and pressure, it has been possible to separate out specific fractions rich in cannabinoids along with the terpenes and flavonoids which can be separated relatively easily to obtain an extract which contains the desirable components in an acceptable form.

Furthermore, very good batch-to-batch reproducibility can be obtained between batches and unwanted constituents, such as waxes, resins or other undesirable compounds which may be present to varying extents in the raw material, can be left behind in the exhausted material.

In another aspect, the invention also relates to a *Cannabis* extract comprising cannabinoid in a range of 30-75%, terpenes 5-35% and flavonoids.

In an embodiment, the *Cannabis* extract is obtained in an yield by mass of 6-20%.

In yet another aspect, the extract may be used in a wide range of applications and can be added as a concentrate in pharmaceuticals, foods, herbal preparations, supplements.

Advantageously, the process as a whole is a set of processes whose significance lies in their combination and specificity, resulting in a refined *Cannabis* extract. The extract is obtained through a single stage of extraction, as opposed to conventional practices including multiple-stage process, and without the use of a secondary solvent based winterization process. Thus, the extract provides a high degree of medically significant plant extract in a stable form.

EXAMPLES

The following experimental examples are illustrative of the invention but not limitative of the scope thereof:

*Cannabis* plant material was cultivated under the medical *Cannabis* laws of the State of California.

The plant material was subjected to pre-extraction processes and prepared to specifications, which included the removal of the non-flower plant components, appropriate moisture level, appropriate process temperature control, etc. Subsequently, the plant material, preferably the flowering part, was ground and loaded into a CO2 extraction machine. The machine was operated within a specific set of parameters which allowed for concentration to take place, and there was an accumulation of "crude" concentrate which was removed from the collection chamber. This material was then loaded into centrifuge tubes, and passed through an initial process of centrifugation, at the beginning of the centrifuge protocol designated. From here, there was a manual separation process to remove the purified oils from the lipids, waxes and water contaminants. Then, further steps of the centrifugation protocol were utilized to more thoroughly and completely refine the concentrate until the process was complete. The resultant concentrate was utilized as per product development goals.

The foregoing description of the invention has been set merely to illustrate the invention and is not intended to be limiting. Since the modifications of the disclosed embodiments incorporating the spirit and substance of the invention may occur to the person skilled in the art, the invention should be construed to include everything within the scope of the disclosure.

What is claimed is:

1. A process for preparing an extract from cannabis, comprising (a) an extraction step of treating the cannabis with carbon dioxide at a temperature of between 0° C. to 15° C. and a pressure between 1250 psi and 1600 psi to obtain an extract;

(b) a decarboxylation step of the extract obtained in step (a) at a temperature between 115° C. and 140° C.;

(c) a centrifuging step of the extract obtained in step (b) at a temperature between 20° C. to 40° C. resulting in a mechanical separation of a concentrate of the extract, wherein the centrifuging step comprises carrying out multiple centrifugation cycles at an RPM of between 5000-12000 for a duration of between 30 minutes and 6 hours per cycle;

(d} a manual separation; and (e) at least one further step of centrifugation to refine the concentrate;

wherein the extract comprises cannabinoid in a range of 30-75%, terpenes 5-35%, and flavonoids, and wherein the process is performed without adding a secondary solvent and without a secondary solvent based winterization step.

* * * * *